US012601697B2

(12) United States Patent
Fuka et al.

(10) Patent No.: US 12,601,697 B2
(45) Date of Patent: *Apr. 14, 2026

(54) SYSTEM AND METHOD FOR PREDICTING THE PRESENCE OF RARE EARTH ELEMENTS

(71) Applicant: Microbeam Technologies, Inc., Grand Forks, ND (US)

(72) Inventors: Matthew Fuka, Grand Forks, ND (US); Eric Kolb, Grand Forks, ND (US); Alexander Benson, Denver, CO (US); Steven Benson, Victoria, MN (US)

(73) Assignee: Microbeam Technologies, Inc., Grand Forks, ND (US)

( * ) Notice: Subject to any disclaimer, the term of this patent is extended or adjusted under 35 U.S.C. 154(b) by 303 days.

This patent is subject to a terminal disclaimer.

(21) Appl. No.: 18/347,826

(22) Filed: Jul. 6, 2023

(65) Prior Publication Data

US 2024/0003836 A1 Jan. 4, 2024

Related U.S. Application Data

(63) Continuation of application No. 17/650,773, filed on Feb. 11, 2022, now Pat. No. 11,733,184.

(Continued)

(51) Int. Cl.
*G01N 23/223* (2006.01)
*G01N 23/222* (2006.01)
*G01N 33/28* (2006.01)

(52) U.S. Cl.
CPC ......... *G01N 23/222* (2013.01); *G01N 23/223* (2013.01); *G01N 33/2858* (2013.01);

(Continued)

(58) Field of Classification Search
CPC .... G01N 23/222; G01N 23/223; G01N 33/28; G01N 33/2858; G01N 2223/0745;

(Continued)

(56) References Cited

U.S. PATENT DOCUMENTS

| | | | |
|---|---|---|---|
| 7,006,919 B2 | 2/2006 | Osucha et al. | |
| 11,733,184 B2 * | 8/2023 | Fuka ................... | G01N 33/2858 |
| | | | 250/358.1 |

(Continued)

OTHER PUBLICATIONS

U.S. Appl. No. 17/650,773, filed Feb. 11, 2022, inventors Fuka et al.

*Primary Examiner* — Jurie Yun
(74) *Attorney, Agent, or Firm* — DeWitt LLP

(57) ABSTRACT

A system for predicting rare earth elements (REEs) in a feedstock sample includes a measurement instrument that records a measurement for a sample, a processor communicatively coupled to the measuring instrument, and a memory communicatively coupled to the processor and containing machine readable instructions that, when executed by the processor, cause the processor to correlate the measurement series using a model; and predict a presence of one or more rare earth element based at least in part on the correlation. A method for predicting rare earth elements includes measuring feedstock samples via XRF or PGNAA, to generate a measurements of elements of interest with a lower atomic weight than REEs; correlating the measurements with a model; and predicting a presence of one or more rare earth elements based at least in part on the correlation.

20 Claims, 5 Drawing Sheets

Related U.S. Application Data

(60) Provisional application No. 63/150,351, filed on Feb. 17, 2021, provisional application No. 63/148,292, filed on Feb. 11, 2021.

(52) U.S. Cl.
CPC ................ *G01N 2223/0745* (2013.01); *G01N 2223/076* (2013.01); *G01N 2223/301* (2013.01); *G01N 2223/305* (2013.01); *G01N 2223/616* (2013.01); *G01N 2223/617* (2013.01)

(58) Field of Classification Search
CPC ....... G01N 2223/076; G01N 2223/301; G01N 2223/305; G01N 2223/616; G01N 2223/617
See application file for complete search history.

(56) References Cited

U.S. PATENT DOCUMENTS

| | | |
|---|---|---|
| 2022/0252530 A1 | 8/2022 | Fuka et al. |
| 2024/0011965 A1* | 1/2024 | Benson .................. G01N 33/24 |

\* cited by examiner

| | Ash | SiO2 | Al2O3 | TiO2 | Fe2O3 | CaO | MgO | K2O | Na2O | SO3 | P2O5 | SrO | BaO | MnO2 |
|---|---|---|---|---|---|---|---|---|---|---|---|---|---|---|
| Ce | 224.23 | 40.08 | 70.21 | 19.25 | 28.91 | 101.94 | 194.00 | 50.32 | 229.90 | 82.11 | 37.58 | 285.12 | 261.17 | 43.32 |
| Dy | 10.08 | 3.40 | 4.68 | 7.92 | 2.82 | 18.70 | 16.76 | 8.63 | 3.95 | 29.05 | 0.79 | 11.05 | 8.25 | 1.80 |
| Er | 5.57 | 2.17 | 2.21 | 6.04 | 1.98 | 16.27 | 6.49 | 4.32 | 0.84 | 17.77 | 0.02 | 13.64 | 7.54 | 0.83 |
| Eu | 3.38 | 0.67 | 0.18 | 2.09 | 0.33 | 3.77 | 4.36 | 1.22 | 4.38 | 6.08 | 0.50 | 3.64 | 1.17 | 0.28 |
| Gd | 14.58 | 3.50 | 4.41 | 6.92 | 1.40 | 9.34 | 26.43 | 9.89 | 14.34 | 28.11 | 2.02 | 10.42 | 3.42 | 2.55 |
| Ga | 63.29 | 29.80 | 33.70 | 12.75 | 2.53 | 33.27 | 7.28 | 4.86 | 25.23 | 16.83 | 3.94 | 45.10 | 40.10 | 6.94 |
| Ge | 10.11 | 13.60 | 4.75 | 26.52 | 5.61 | 51.11 | 23.95 | 10.97 | 21.89 | 43.27 | 6.48 | 57.65 | 51.14 | 9.76 |
| Ho | 1.86 | 0.68 | 0.89 | 1.79 | 0.65 | 4.59 | 2.90 | 1.68 | 0.02 | 5.90 | 0.05 | 3.76 | 2.05 | 0.28 |
| La | 117.81 | 23.16 | 42.71 | 2.97 | 19.32 | 89.93 | 78.05 | 19.38 | 124.57 | 35.65 | 17.19 | 142.93 | 145.52 | 20.29 |
| Lu | 0.86 | 0.32 | 0.08 | 1.07 | 0.28 | 1.75 | 0.92 | 0.45 | 0.16 | 2.22 | 0.09 | 1.21 | 0.90 | 0.11 |
| Mo | 4.19 | 24.97 | 4.81 | 14.62 | 14.59 | 100.28 | 20.93 | 13.63 | 35.93 | 63.26 | 11.33 | 107.06 | 49.08 | 2.68 |
| Nd | 97.08 | 19.12 | 24.12 | 20.46 | 6.75 | 23.29 | 117.49 | 27.64 | 94.92 | 41.45 | 17.72 | 132.88 | 87.67 | 17.26 |
| Pr | 26.29 | 6.18 | 7.77 | 4.30 | 2.46 | 1.29 | 26.16 | 6.25 | 24.97 | 10.45 | 4.44 | 33.63 | 24.80 | 4.70 |
| Sm | 18.26 | 3.37 | 4.13 | 6.00 | 0.22 | 2.94 | 27.59 | 8.54 | 18.45 | 18.51 | 3.22 | 22.81 | 10.13 | 2.99 |
| Sc | 41.41 | 23.50 | 5.50 | 30.14 | 3.43 | 28.55 | 4.30 | 6.89 | 7.91 | 31.55 | 4.13 | 0.27 | 15.56 | 1.11 |
| Tb | 1.96 | 0.49 | 0.78 | 1.13 | 0.36 | 2.96 | 3.32 | 1.57 | 1.08 | 4.86 | 0.14 | 0.77 | 0.42 | 0.31 |
| Th | 0.82 | 0.29 | 0.24 | 0.93 | 0.28 | 1.96 | 0.96 | 0.59 | 0.05 | 2.35 | 0.04 | 1.74 | 1.08 | 0.11 |
| Yb | 20.41 | 18.01 | 25.75 | 60.82 | 27.92 | 605.98 | 166.76 | 90.34 | 74.41 | 591.10 | 15.26 | 62.61 | 31.11 | 43.63 |
| Yt | 21.28 | 34.62 | 12.84 | 126.06 | 6.58 | 395.19 | 103.12 | 49.34 | 77.31 | 389.67 | 11.59 | 92.19 | 107.83 | 38.59 |
| LREE | 528.47 | 116.08 | 154.27 | 79.27 | 53.46 | 199.25 | 443.34 | 106.48 | 505.09 | 225.82 | 84.77 | 620.75 | 514.89 | 89.94 |
| HREE | 77.43 | 27.47 | 26.19 | 91.05 | 29.10 | 266.34 | 121.42 | 68.13 | 15.72 | 291.70 | 0.52 | 176.55 | 93.53 | 11.02 |
| TREE | 605.90 | 143.56 | 180.46 | 170.32 | 24.35 | 465.60 | 564.76 | 174.60 | 520.81 | 517.52 | 84.26 | 444.20 | 421.36 | 100.96 |

FIG. 1

| | Sc | Y | La | Ce | Pr | Nd | Sm | Eu | Gd | Tb | Dy | Ho | Er | Tm | Yb | Lu |
|---|---|---|---|---|---|---|---|---|---|---|---|---|---|---|---|---|
| Ash Content% | 12.5 | 112.1 | 87.7 | 192.2 | 18.0 | 84.9 | 14.8 | 2.8 | 15.6 | 2.8 | 16.6 | 2.9 | 9.7 | 0.7 | 8.9 | 0.6 |
| Ash Content%^ | 0.3 | 154.6 | 21.9 | 100.6 | 24.1 | 27.0 | 18.9 | 0.8 | 20.6 | 102.6 | 22.8 | 1.4 | 24.6 | 1.5 | 0.1 | 1.5 |
| NaKa1 | 18.6 | 11.9 | 181.1 | 382.0 | 67.1 | 227.5 | 55.7 | 11.7 | 46.0 | 5.6 | 20.9 | 0.0 | 2.9 | 0.2 | 1.5 | 0.5 |
| MgKa1 | 36.2 | 69.9 | 91.6 | 240.1 | 41.6 | 128.2 | 38.0 | 8.5 | 36.3 | 5.0 | 24.3 | 3.4 | 12.1 | 1.3 | 6.8 | 0.9 |
| AlKa1 | 55.7 | 71.8 | 126.7 | 256.2 | 32.5 | 154.5 | 30.2 | 9.9 | 27.1 | 5.8 | 24.9 | 3.7 | 10.2 | 1.8 | 7.5 | 1.9 |
| Al^ | 2.5 | 23.0 | 17.1 | 38.0 | 1.4 | 22.8 | 1.3 | 2.6 | 1.4 | 2.5 | 7.1 | 24.2 | 0.6 | 0.7 | 17.7 | 0.7 |
| SiKa1 | 217.5 | 376.6 | 197.9 | 217.5 | 22.7 | 171.7 | 20.1 | 4.8 | 31.7 | 7.9 | 71.3 | 0.7 | 24.5 | 0.0 | 15.4 | 2.5 |
| Sr^ | 0.7 | 58.0 | 36.5 | 134.7 | 41.0 | 47.3 | 6.1 | 1.6 | 18.6 | 0.1 | 0.5 | 1.9 | 1.9 | 1.1 | 0.0 | 1.8 |
| P Ka1 | 13.1 | 35.9 | 91.2 | 168.2 | 22.5 | 115.5 | 15.8 | 2.3 | 7.0 | 0.7 | 1.4 | 3.8 | 8.0 | 1.9 | 2.9 | 1.3 |
| S Ka1 | 82.6 | 150.9 | 172.9 | 377.0 | 15.8 | 207.1 | 19.7 | 6.7 | 18.3 | 4.2 | 19.6 | 6.0 | 9.2 | 1.7 | 7.6 | 1.2 |
| K Ka1 | 35.6 | 109.0 | 33.1 | 82.7 | 13.0 | 30.6 | 11.3 | 2.9 | 16.7 | 2.8 | 18.0 | 3.3 | 11.8 | 1.4 | 10.1 | 1.4 |
| CaKa1 | 47.2 | 64.6 | 294.1 | 421.9 | 15.1 | 298.2 | 7.9 | 0.2 | 2.5 | 1.3 | 15.8 | 7.2 | 12.5 | 2.9 | 9.3 | 2.4 |
| Ca^ | 0.2 | 0.0 | 0.6 | 0.6 | 80.1 | 0.6 | 17.9 | 13.3 | 1.6 | 14.3 | 295.5 | 25.0 | 20.9 | 1.9 | 2.0 | 2.0 |
| TiKa1 | 2545.7 | 5017.1 | 6596.7 | 14300.3 | 2181.9 | 7651.6 | 1890.1 | 442.3 | 1855.8 | 255.7 | 1314.9 | 123.9 | 527.3 | 57.1 | 289.7 | 50.0 |
| Ti^ | 29.1 | 28.3 | 32.1 | 133.0 | 68.8 | 40.7 | 63.8 | 0.1 | 24.0 | 16.8 | 3.7 | 0.0 | 0.2 | 0.4 | 0.2 | 0.4 |
| FeKa1 | 101.7 | 158.5 | 98.9 | 165.7 | 53.0 | 90.2 | 39.2 | 8.5 | 43.8 | 5.3 | 29.5 | 3.1 | 14.1 | 1.1 | 11.8 | 1.0 |
| Fe^ | 32.1 | 28.6 | 30.8 | 115.9 | 23.7 | 38.6 | 17.1 | 21.3 | 20.9 | 17.9 | 18.8 | 56.1 | 30.4 | 2.8 | 37.7 | 1.2 |
| BaKa1 | 17.6 | 4.3 | 11.4 | 8.0 | 1.8 | 7.6 | 0.3 | 0.9 | 3.4 | 0.3 | 3.2 | 0.4 | 3.7 | 0.0 | 7.2 | 0.8 |
| BaLa1 | 2241.8 | 4702.4 | 6083.6 | 13326.4 | 1928.1 | 7091.1 | 1696.9 | 399.0 | 1669.9 | 235.3 | 1215.1 | 136.9 | 492.9 | 56.1 | 248.4 | 48.6 |
| SrKa1 | 23.6 | 43.3 | 48.8 | 114.2 | 17.2 | 61.8 | 15.4 | 3.6 | 15.5 | 2.3 | 12.2 | 2.0 | 6.4 | 0.7 | 4.4 | 0.6 |
| MnKa1 | 18.9 | 76.6 | 50.4 | 95.9 | 4.1 | 40.3 | 6.3 | 2.7 | 9.7 | 1.4 | 13.3 | 2.9 | 18.3 | 1.1 | 7.5 | 1.0 |
| Mn^ | 4.3 | 63.4 | 38.6 | 148.1 | 23.0 | 51.0 | 7.6 | 9.9 | 2.0 | 1.6 | 26.2 | 1.6 | 0.2 | 1.5 | 1.5 | 1.5 |
| GaKa1 | 1.7 | 10.9 | 481.0 | 1273.8 | 146.2 | 733.3 | 138.3 | 32.8 | 89.7 | 12.4 | 48.0 | 0.0 | 5.6 | 2.6 | 16.3 | 4.3 |
| Y Ka1 | 57.9 | 139.6 | 118.3 | 292.6 | 32.6 | 159.2 | 32.5 | 8.5 | 31.7 | 5.1 | 27.7 | 5.1 | 12.6 | 1.5 | 10.3 | 1.4 |
| LaLa1 | 677.8 | 1028.5 | 1413.9 | 2885.8 | 571.4 | 1574.6 | 461.9 | 101.3 | 452.0 | 56.4 | 283.8 | 0.0 | 111.1 | 11.1 | 79.2 | 11.2 |
| CeLa1 | 121.9 | 374.0 | 152.2 | 316.8 | 24.6 | 139.5 | 30.6 | 12.4 | 44.6 | 10.8 | 59.0 | 13.2 | 30.2 | 3.9 | 0.0 | 3.4 |
| NdLa1 | 13.7 | 114.9 | 1049.2 | 2502.7 | 404.7 | 1414.0 | 344.4 | 69.8 | 270.6 | 28.2 | 108.4 | 0.0 | 6.4 | 0.2 | 5.2 | 2.9 |

FIG.2A

| | HREE | LREE | Total REE | LREE/HREE |
|---|---|---|---|---|
| Ash Content % | 155.5 | 437.0 | 646.1 | 2.4 |
| Ash Content %^ | 106.4 | 382.1 | 604.4 | 133.2 |
| NaKa1 | 72.0 | 955.0 | 1025.3 | 0.6 |
| MgKa1 | 174.6 | 559.7 | 806.8 | 12.4 |
| AlKa1 | 118.5 | 626.5 | 787.7 | 18.8 |
| Al^ | 2.7 | 103.0 | 116.4 | 2.4 |
| SiKa1 | 497.3 | 701.1 | 333.1 | 246.3 |
| Si^ | 76.1 | 610.9 | 1031.0 | 40.8 |
| P Ka1 | 123.8 | 427.6 | 15.9 | 21.8 |
| S Ka1 | 172.2 | 953.9 | 1127.4 | 46.8 |
| K Ka1 | 210.3 | 160.9 | 358.3 | 2.0 |
| CaKa1 | 187.6 | 1087.0 | 467.2 | 84.7 |
| Ca^ | 11.1 | 0.8 | 0.7 | 0.4 |
| TiKa1 | 11240.5 | 33625.5 | 44646.4 | 485.6 |
| Ti^ | 73.3 | 659.8 | 1141.5 | 1.5 |
| FeKa1 | 396.9 | 379.5 | 758.1 | 45.2 |
| Fe^ | 69.5 | 512.2 | 857.6 | 1.8 |
| BaKa1 | 88.9 | 24.2 | 190.7 | 14.9 |
| BaLa1 | 10159.2 | 31339.6 | 41418.8 | 589.0 |
| SrKa1 | 94.6 | 268.5 | 362.9 | 1.6 |
| MnKa1 | 122.5 | 215.7 | 315.9 | 8.4 |
| Mn^ | 75.9 | 788.2 | 1363.8 | 2.0 |
| GaKa1 | 330.2 | 3036.6 | 3297.6 | 24.1 |
| Y Ka1 | 214.0 | 696.2 | 973.5 | 40.8 |
| LaLa1 | 2741.7 | 6746.9 | 9333.2 | 48.6 |
| CeLa1 | 525.7 | 803.6 | 1717.5 | 3.0 |
| NdLa1 | 263.9 | 5865.8 | 6032.1 | 199.5 |

FIG. 2B

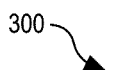

300

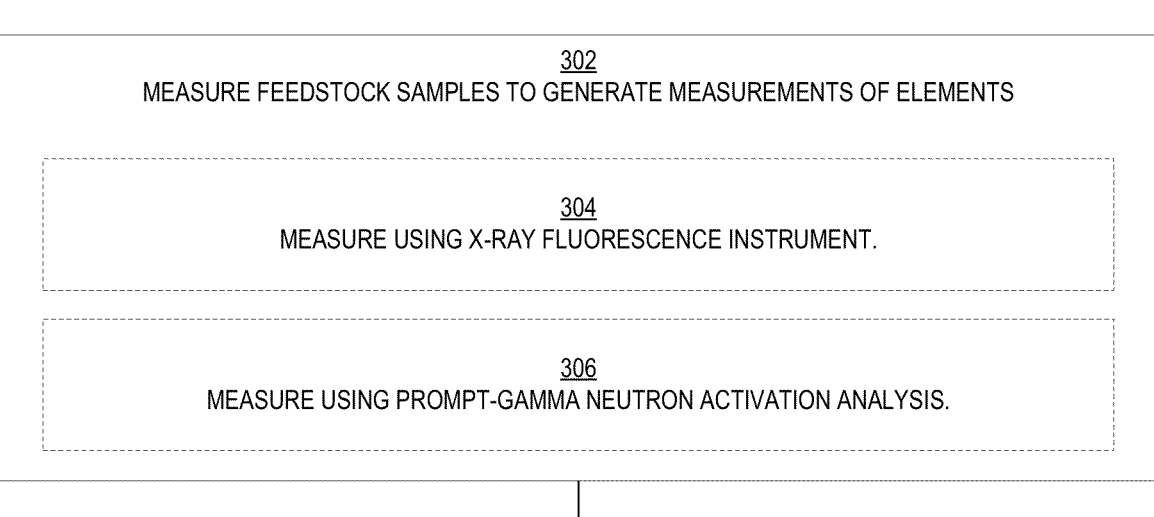

302
MEASURE FEEDSTOCK SAMPLES TO GENERATE MEASUREMENTS OF ELEMENTS

304
MEASURE USING X-RAY FLUORESCENCE INSTRUMENT.

306
MEASURE USING PROMPT-GAMMA NEUTRON ACTIVATION ANALYSIS.

308
CORRELATE THE MEASUREMENTS USING A MODEL.

310
THE MODEL INCLUDES A CORRESPONDING FITTING CONSTANT FOR EACH ELEMENT OF INTEREST.

312
PREDICT PRESENCE OF ONE OR MORE RARE EARTH ELEMENTS.

314
THE RARE EARTH ELEMENT INCLUDES ONE OR MORE OF TOTAL RARE EARTH ELEMENT, LIGHT RARE EARTH ELEMENT, HEAVY RARE EARTH ELEMENT, AND THE RATIO OF LIGHT RARE EARTH ELEMENT TO HEAVY RARE EARTH ELEMENT.

| SAMPLE 420 | ← | INSTRUMENT 410 | ↔ | PROCESSOR 430 |

MEMORY 440

INSTRUCTIONS 442

PREDICTIONS 448

MODEL 444

FITTING CONSTANTS 446

FITTING CONSTANTS 447

MEASUREMENT DATA 450

ASH CONTENT DATA 452

SYSTEM AND METHOD FOR PREDICTING THE PRESENCE OF RARE EARTH ELEMENTS

RELATED APPLICATIONS

This application is a continuation of U.S. application Ser. No. 17/650,773 filed Feb. 11, 2022, which claims priority to U.S. Provisional Application No. 63/148,292 filed Feb. 11, 2021, and U.S. Provisional Application No. 63/150,351 filed Feb. 17, 2021, both of which are incorporated herein in their entirety by reference.

GOVERNMENTAL INTEREST

This application was developed in association with the U.S. Department of Energy under Contract No. DE-SC0021837. The U.S. Government has certain rights in this application.

BACKGROUND

Rare earth elements (REE) are crucial materials in many electronic devices, energy system components and military defense applications. The rare earth group of elements includes lanthanum (La), cerium (Ce), praseodymium (Pr), neodymium (Nd), samarium (Sm), europium (Eu), gadolinium (Gd), scandium (Sc), yttrium (Y), terbium (Tb), dysprosium (Dy), holmium (Ho), erbium (Er), thulium (Tm), ytterbium (Yb), and lutetium (Lu). REE include light rare earth elements (LREE) and heavy rare earth elements (HREE). LREE include lanthanum, cerium, praseodymium, neodymium, samarium, europium, and gadolinium. HREE include scandium, yttrium, terbium, dysprosium, holmium, erbium, thulium, ytterbium, and lutetium. Other elements experiencing increasing demand in the production of high-tech devices include gallium and germanium. Locating these elements in feedstock and mined materials can be challenging.

Recently, coal and coal byproducts have been identified as a promising sources of REE. However, methods for detecting these elements in a feedstock sample in the field are limited. It is often necessary to bring samples to laboratory-based equipment that is expensive and non-portable. One lab-based method for detecting and measuring REE in samples is inductively-coupled plasma optical emission spectroscopy (ICP-OES), which require expensive instrumentation that is not fit for deployable use near mining sites.

SUMMARY OF THE INVENTION

In a first aspect, a system and method predict REE levels in a feedstock without requiring direct measurement of the REEs. Sensors are combined with predictive algorithms to enable selective mining and sorting of high rare earth element (REE) content coal and coal-related feedstocks. In embodiments, sensors may be incorporated in stationary and handheld devices that may be used in a wide variety of locations, such as a mining site or feedstock processing facility.

A method for predicting the presence of rare earth elements (REEs) in a feedstock includes measuring a feedstock sample using a spectrum analyzer to generate measurements of elements of interest with a lower atomic weight than REEs; correlating the measurements with a model; and predicting presence of one or more REEs based at least in part on the correlation.

A system for predicting the presence of rare earth elements in a feedstock includes a measuring instrument that records a measurement for a feedstock sample; a processor, communicatively coupled to the measuring instrument; and a memory communicatively coupled to the processor and containing machine readable instructions that, when executed by the processor, causes the processor to execute the method.

Sensors may include elemental analyzers such as X-ray fluorescence (XRF) analyzers and prompt gamma neutron activation analysis (PGNAA) sensors, which identify REE-rich layers in coal seams using a relatively simple and inexpensive sensor technology. XRF is fast and field deployable and can be employed in combination with selective mining and real-time on-belt coal sorting using PGNAA to provide more efficient identification of REE-rich feedstocks.

BRIEF DESCRIPTION OF THE FIGURES

FIG. 1 is a table of constants for use with a model for predicting the presence of rare earth elements (REEs), in embodiments.

FIGS. 2A-2B are tables of constants for use with another model for predicting the presence of REEs, in embodiments.

FIG. 3 is a flowchart illustrating a method for predicting the presence of REEs, in embodiments.

DETAILED DESCRIPTION OF THE EMBODIMENTS

Figure 4:
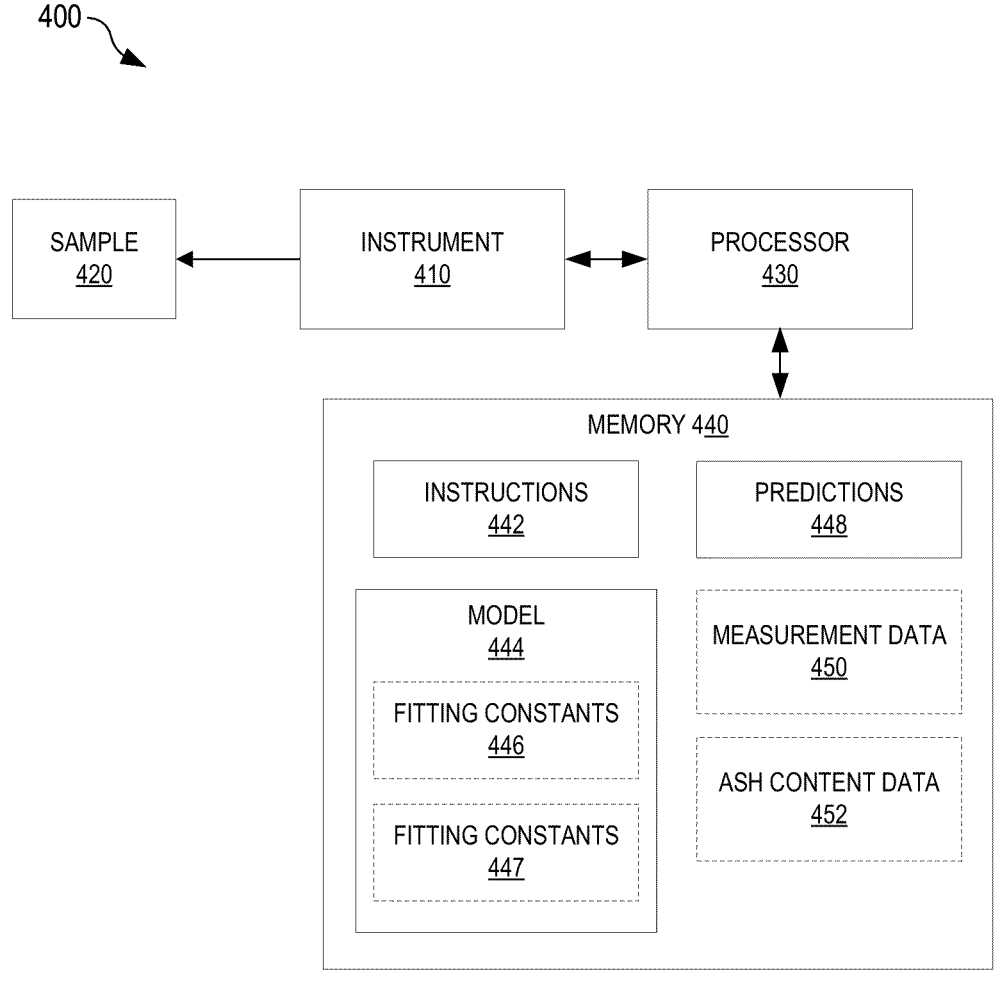
FIG. 4 shows a system for predicting the presence of REEs, in embodiments.

Spectral analysis can be used to identify the presence and quantity, or abundance, of elements in a feedstock, such as coal and coal byproducts. X-ray fluorescence (XRF) identifies elements by irradiating a sample with high-energy X-rays and capturing the resulting fluorescence with a spectrum analyzer. Each element in the sample will exhibit a characteristic fluorescence signature, which can be used to identify the element and its abundance in the sample.

Another technique for spectral analysis is prompt-gamma neutron activation analysis (PGNAA), which irradiates a sample with a beam of neutrons. Elements in the sample will emit gamma rays with can be measured with a gamma ray spectrometer. While similar, XRF and PGNAA may capture different information. For example, XRF measures limited depths and surface areas whereas PGNAA is able to penetrate an entire cross-section of a sample. A spectrum captured by spectral analysis of a sample is typically shown as wavelength vs. count rate, or number of emissions per second, for example. A graph of the spectrum will show peaks at various wavelengths, which can be associated elements in the sample.

Identifying the REE presence and abundance in a sample is best done as close to the mining process as possible. Since REEs are rare, not all mined feedstocks contain any REEs or enough to justify extraction. Mixing of feedstocks during transport and/or processing can dilute the concentration of REEs, which makes identification close to the point of mining i.e., before a quantity of ore has been intermixed with other ore, beneficial. REEs are among the heaviest atoms in the periodic table. Thus, detecting REEs with spectral analysis requires irradiating a sample with higher energy particles to generate emissions that can be captured with a spectrometer. Providing these higher energy particles can be difficult or impossible in the field or at locations, where identifying REE content of a sample provides the best information for further processing. Embodiments are discussed herein in terms of identifying REEs but other elements may also be identified, such as gallium and germanium. Any reference to REE should be understood to also refer at least to gallium and germanium.

In embodiments, a method of predicting REE presence and abundance uses spectral analysis of a sample to detect key elements which are quantifiable by XRF and/or PGNAA. Measurements of these elements are then used to predict REEs by a model that correlates presence of the key elements with presence of REEs. Table 1 shows REEs that are predicted using embodiments discussed herein in the left column. Elements that are measured using XRF are shown in the center column and elements that are measured using PGNAA are shown in the right column.

TABLE 1

| Predicted REE | XRF | PGNAA |
|---|---|---|
| La | Na | $Al_2O_3$ |
| Ce | Mg | CaO |
| Pr | Al | $Fe_2O_3$ |
| Nd | Si | $K_2O$ |
| Pm | P | MgO |
| Sm | K | $MnO_2$ |
| Eu | Ca | $Na_2O$ |
| Gd | Ti | $SiO_2$ |
| Tb | Fe | $SO_3$ |
| Dy | Ba | $TiO_2$ |
| Ho | Mn | |
| Er | Sr | |
| Tm | | |
| Yb | | |
| Lu | | |
| Ge | | |
| Ga | | |

XRF and PGNAA methods produce a spectrum from a sample. From the spectrum, the peaks are separated from the background (valleys/parts of the curves outside of the peaks). The peak areas are used to provide elemental compositions of a sample based on standard compositions. When XRF and PGNAA analyzers provide an output for elemental measurements, there are calibrations and algorithms used to process this peak area data to output a final number for the amount of the element associated with each peak. The final elemental output measurement may be used to make statistical correlations between elements and REE.

In embodiments, the full raw spectra captured by XRF or PGNAA is used instead of the calculated elemental measurements. A model is built, or trained, using samples with known REE presence and abundance to generate coefficients incorporating the background as well as the peaks of a spectrum. The background can also be understood as the valleys between peaks. While coefficients are labeled with an element such as "Na, K, Ca, etc." herein, the coefficients are not the final elemental output measurements but the raw spectral values (including some of the background). As further samples are processed, neural networks or other computational analysis techniques may be used to continue to develop the model algorithms using the original, or training, coefficients.

A general form of the model is represented as follows. Measurements made by spectral analysis, either XRF or PGNAA, may include a measurement series having a plurality of y individual XRF measurements, $m_1, m_2, \ldots m_y$. The model also includes a set of x predictions $p_1, p_2, \ldots p_x$, for REE abundance predictions of x REE species. Each prediction uses y fitting constants C, one for each individual measurement m, such that $$p_1 = m_1 * C1_1 + m_2 * C1_2 + \ldots + m_y * C1_y \qquad (1)$$

$$p_2 = m_1 * C2_1 + m_2 * C2_2 + \ldots + m_y * C2_y \qquad (2)$$

$$\ldots$$

$$p_x = m_1 * Cx_1 + m_2 * Cx_2 + \ldots + m_y * Cx_y. \qquad (3)$$

The value of each fitting constant is variable and is fit based on a measured abundance for each REE using a complementary technique, for example ICP-OES. The set of all y*x=N fitting constants can be fit using a training set where the measured abundance of each of the x REE species is known experimentally. The model, using these fitting constants, is then used to predict the presence of one or more of the x REE species using a measurement series recorded for a new sample. In embodiments, a neural network may be used to generate the model.

FIG. 1 is a table of constants for use with the model represented by equations (1)-(3) for measurements generated using PGNAA. FIG. 2A is a table of constants for use with the model represented by equations (1)-(3) for measurements generated using XRF. FIG. 2B is a table of measurements from FIG. 2A for HREE, LREE, total REE and LREE/HREE. The specific constants shown in FIGS. 1, 2A and 2B are to illustrate principles disclosed herein and other constants and elements may be used. The rows illustrate represent a set of constants $C1_1, C1_2, \ldots C1_y$ for an REE species x. The columns represent a set of constants $C1_1, C2_1, \ldots Cx_1$ for a measured element. Each cell indicates the value of a given constant after fitting to a set of samples with REE values measured with ICP-OES. Cells in boldface type are in the top 25% of measurements to the REE prediction and cells in italic are in the bottom 25%. Any measured sample may include a subset of the elements shown in FIGS. 1, 2A and 2B, as well as additional elements. Further, any REE of interest may be predicted from a subset of the elements shown in FIGS. 1 and 2, or from additional elements.

In an embodiment, the model described above includes using the fitting coefficients as exponents in addition to multipliers. For example, given the same individual measurements $m_1, m_2, \ldots m_y$, a set of prediction $p_1, p_2, \ldots p_x$ is calculated using two sets of fitting coefficients C and D, both having y*x=N coefficients in the set, such that $$p_1 = C1_1 * (m_1)^{D1_1} + C1_2 * (m_2)^{D1_2} + \ldots + C1_y * (m_y)^{D1_y} \qquad (4)$$

$$p_2 = C2_1 * (m_1)^{D2_1} + C2_2 * (m_2)^{D2_2} + \ldots + C2_y * (m_y)^{D2_y} \qquad (5)$$

$$\ldots$$

$$p_x = Cx_1 * (m_1)^{Dx_1} + Cx_2 * (m_2)^{Dx_2} + \ldots + Cx_y * (m_y)^{Dx_y}. \qquad (6)$$

In an embodiment, each measurement is normalized to a value between zero and one based at least in part on a peak-value measured for that measurement of the measurement series.

In an embodiment, the predicted abundances include one or more of total rare earth element, light rare earth element, heavy rare earth element, the ratio of light rare earth element to heavy rare earth element, lanthanum, cerium, praseodymium, neodymium, samarium, europium, gadolinium, scandium, yttrium, terbium, dysprosium, holmium, erbium, thulium, ytterbium, and lutetium.

FIG. 3 is a flowchart illustrating a method 300 for predicting the presence and abundance of rare earth elements. Method 300 may include blocks 302, 308 and 312. In embodiments, the block 302 includes one of blocks 304 or 306, block 308 includes block 310, and block 312 includes block 314.

In block 302, feedstock samples are measured to generate measurements of elements of interest in the sample. In an example of block 302, elements of interest are measured using a spectrum analyzer and include elements that have a lower atomic weight than rare earth elements. Block 304 includes measuring the feedstock sample using x-ray fluorescence. Block 306 includes measuring the feedstock sample using prompt-gamma neutron activation analysis. Embodiments discussed herein may use either or both types of spectrum analysis.

In block 308, the measurements are correlated using a model. In block 310, the model includes a corresponding fitting constant for each element of interest. In an example of block 310, the fitting constants are similar to those shown in FIGS. 1 and 2.

In block 312 the presence of one or more rare earth elements is predicted based at least in part on the model correlation. In block 314, the rare earth elements may include one or more of total rare earth element, light rare earth elements, heavy rare earth elements, and the ratio of light rare earth elements to heavy rare earth elements. In an example of blocks 312 and 314, the processor 130 predicts the presence of rare earth elements based at least in part on the correlation of spectrum analyzer measurements of a feedstock sample with coefficients of the model.

The method 300 is not limited, unless otherwise specified or understood by those of ordinary skill in the art, to the order shown in FIG. 3.

FIG. 4 illustrates a system 400 for predicting the abundance of rare earth elements using measuring instrument 410, a processor 430, and a memory 440. The memory includes instructions 442, model 444, and predictions 448. The measuring instrument 410 records a measurement series of a feedstock sample 420 to generate corresponding measurement data 450 that, in an embodiment, is stored in memory 440. The instructions 442, when executed by the processor 430 cause the processor 430 to correlate the measurement series using the model 444 to generate predictions 448. The processor 430 then predicts the presence of one or more rare earth elements based at least in part on the predictions 448. In an embodiment, measuring instrument 410 is a handheld X-ray fluorescence instrument (XRF). In an embodiment, measuring instrument 410 is a prompt gamma neutron activation analysis (PGNAA) sensor.

In an embodiment, the model 444 includes a plurality of fitting constants 446 that include one fitting constant 446 for each measurement of a measurement series. Each fitting constant 446 is multiplied by the corresponding measurement. In an embodiment, one or more of the measurements is raised to the respective power of the corresponding fitting constant.

In an embodiment, the model 444 includes a plurality of fitting constants 447 that include fitting constant 447 for ash content data. Each fitting constant 447 is multiplied by a corresponding measurement of ash content data. In an embodiment, one or more of the measurements is raised to the respective power of the corresponding fitting constant.

In an embodiment, the measuring instrument 410 records a measurement of the sample 420 that includes an abundance measurement of elements of interest, which may include one or more of sodium, magnesium, aluminum, silicon, phosphorus, sulfur, potassium, calcium, titanium, iron, barium, strontium, manganese and yttrium. In embodiments, other elements may be measured. Measuring instrument 410 may record a single measurement from sample 420, or a series of measurements. In an embodiment, the measurement data 450 of sample 420 recorded by measurement instrument 410 is combined with ash content data 452. The instructions 442, when executed by the processor 430 cause the processor 430 to correlate the measurement data 450 and ash content data 452 using the model 444 that includes fitting constants 446 and fitting constants 447 to generate predictions 448. The processor 430 then predicts the presence of one or more rare earth elements based at least in part on the predictions 448.

In an embodiment, the measuring instrument 410 records a measurement of the sample 420 that includes an abundance measurement of silicon, titanium and barium. By including fewer species in the measurement series, system 400 is more efficient in one or more of energy consumption, time, and processing power.

In an embodiment, measuring instrument 410 is a prompt gamma neutron activation analysis (PGNAA) sensor that is communicatively coupled to the processor 430 and that records a measurement of sample 420 to generate corresponding measurement series data 450, that in an embodiment is stored in memory 440. The sample 420 may be present on a conveyor belt and the system 400 measuring instrument 410 can be operated in combination with selective mining to perform real-time on-belt coal sorting.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A system for predicting the presence of rare earth elements (REEs) in a feedstock, comprising:
   a spectrum analyzer operably configured to measure a sample of the feedstock and record a measurement data for the feedstock sample;
   a processor communicatively coupled to the spectrum analyzer, the processor configured to process the measurement data; and
   a memory assembly communicatively coupled to the spectrum analyzer and the processor, the memory assembly comprising one or more machine readable instructions, one or more models, and one or more predictions;
   wherein the one or more instructions, when executed by the processor, cause the processor to measure the feedstock sample using the spectrum analyzer to generate the measurement data corresponding to elements of interest with a lower atomic weight than REEs, correlate the measurement data using the one or more models, and predict the presence of one or more REEs based at least in part on the correlation.

2. The system of claim 1, wherein the spectrum analyzer is an X-ray fluorescence instrument.

3. The system of claim 2, wherein the elements of interest include one or more of sodium, magnesium, aluminum, silicon, phosphorous, potassium, calcium, titanium, iron, barium, manganese and strontium.

4. The system of claim 3, wherein the one or more models comprises a corresponding fitting constant for each element of interest.

5. The system of claim 1, wherein the spectrum analyzer is a hand-held X-ray fluorescence instrument.

6. The system of claim 1, wherein the spectrum analyzer is a prompt gamma neutron activation analysis (PGNAA) sensor.

7. The system of claim 6, wherein the elements of interest include one or more of $Al_2O_3$, $CaO$, $Fe_2O_3$, $K_2O$, $MgO$, $MnO_2$, $Na_2O$, $SiO_2$, $SO_3$ and $TiO_2$.

8. The system of claim 7, wherein the one or more models comprises a corresponding fitting constant for each element of interest.

9. The system of claim 1, wherein the one or more models comprises a corresponding fitting constant for each element of interest.

10. The system of claim 9, wherein the one or more models comprises an ash fitting constant corresponding to an ash content.

11. The system of claim 9, wherein the elements of interest include one or more of sodium, magnesium, aluminum, silicon, phosphorous, sulfur, potassium, calcium, iron, strontium, manganese and yttrium.

12. The system of claim 9, wherein the elements of interest include one or more of silicon, titanium, barium and gallium.

13. The system of claim 1, wherein the REEs comprise one or more of total rare earth elements, light rare earth elements, heavy rare earth elements, and a ratio of light rare earth elements to heavy rare earth elements.

14. The system of claim 1, wherein the feedstock further comprises coal and coal byproducts.

15. The system of claim 14, wherein the coal byproducts further comprise ash content.

16. The system of claim 1, wherein the spectrum analyzer is operably located a conveyor belt, and wherein the conveyor belt is configured to transport the feedstock from a first location to a second location.

17. The system of claim 16, wherein the feedstock is coal and coal byproducts and the spectrum analyzer is configured to perform real-time on-belt coal sorting based upon the prediction of one or more REEs in the feedstock sample.

18. The system of claim 1, wherein the spectrum analyzer captures a full raw spectra from the feedstock sample that comprises the elements of interest.

19. The system of claim 1, wherein the REEs comprise one or more of lanthanum, cerium, praseodymium, neodymium, promethium, samarium, europium, gadolinium, terbium, dysprosium, holmium, erbium, thulium, ytterbium, lutetium, yttrium, scandium, germanium and gallium.

20. The system of claim 1, wherein the measurement data is configured to be stored in the memory assembly.

* * * * *